United States Patent [19]

McClenny et al.

[11] Patent Number: 5,604,348

[45] Date of Patent: Feb. 18, 1997

[54] MEASUREMENT OF ACID SULFATE LEVELS IN AEROSOLS

[75] Inventors: William A. McClenny, Raleigh; Kenneth J. Krost, Cary, both of N.C.

[73] Assignee: United States of America as represented by the Administrator of the U.S. Environmental Agency, Washington, D.C.

[21] Appl. No.: 432,729

[22] Filed: May 2, 1995

[51] Int. Cl.⁶ .................................................. G01N 21/35
[52] U.S. Cl. ........................ 250/341.1; 250/304; 250/435
[58] Field of Search ............................... 250/339.12, 435, 250/304, 341.1

[56] References Cited

U.S. PATENT DOCUMENTS

| | | | |
|---|---|---|---|
| 4,140,005 | 2/1979 | Kittelson | 73/28 |
| 4,392,388 | 7/1983 | Baverle | 73/863.23 |
| 4,823,009 | 4/1989 | Biemann et al. | 250/341 |
| 4,942,297 | 7/1990 | Johnson et al. | 250/304 |
| 4,942,774 | 7/1990 | McFarland | 73/864.81 |

OTHER PUBLICATIONS

McClenny et al, "Speciation of Ambient Sulfate Particulate Matter Using FT–IR–Based Absorption to Complement Wet Chemical and Thermal Speciation Measurements", Applied Spectroscopy, 48 (6), 1994, pp. 706–712.

*Primary Examiner*—Carolyn E. Fields
*Attorney, Agent, or Firm*—Irving M. Freedman

[57] ABSTRACT

A non-destructive unambiguous method of measuring the presence and level of acid sulfates, particularly ammonium bisulfate in air is disclosed including infrared energy absorbance measurements of particles deposited on the filter through which the air passes.

13 Claims, 4 Drawing Sheets

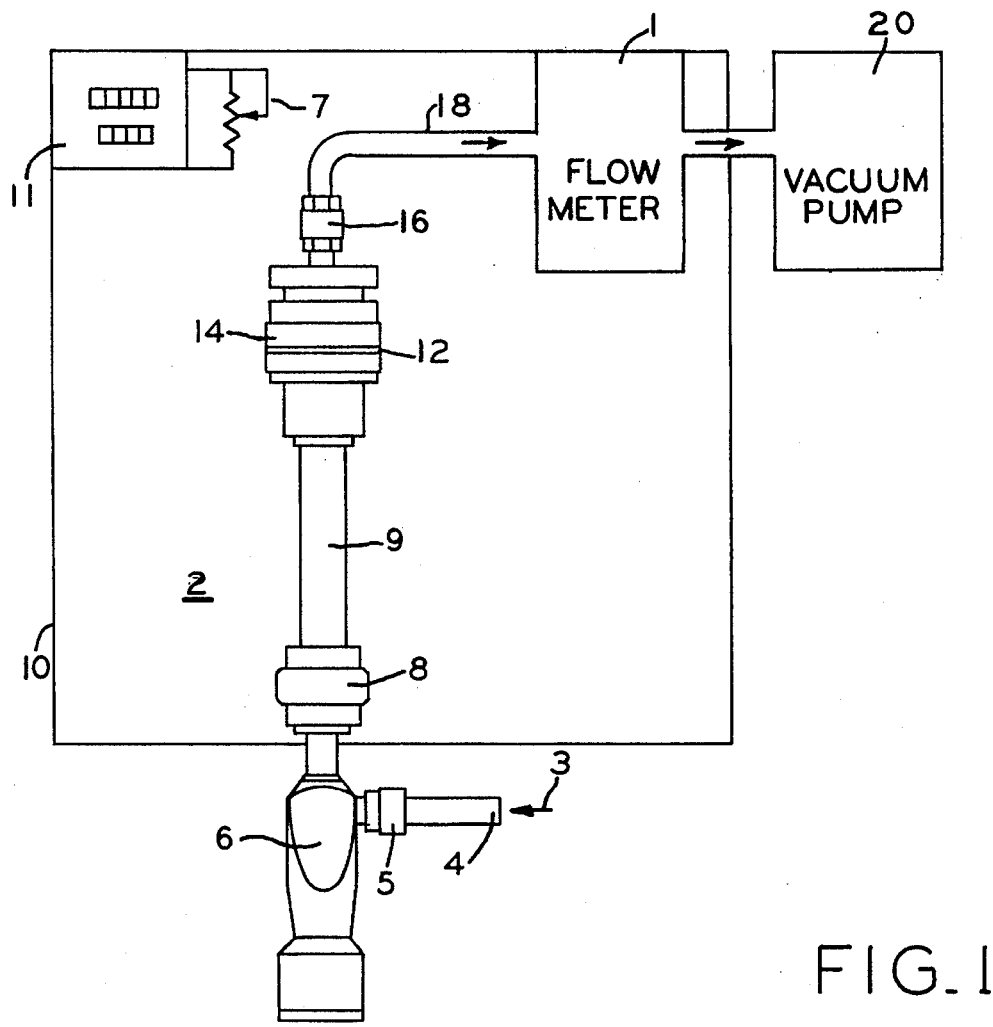
FIG_1
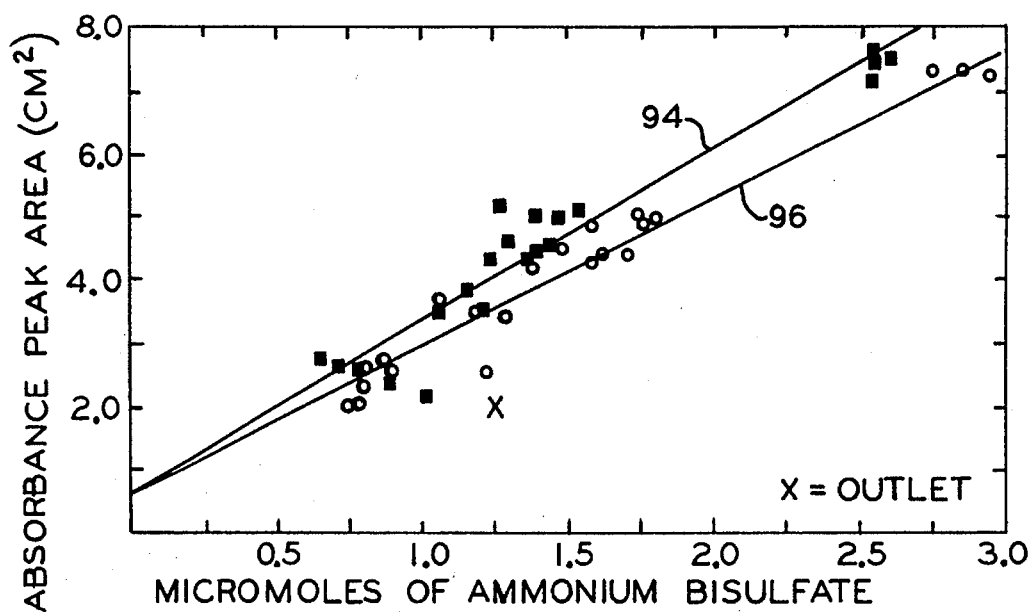
FIG_6

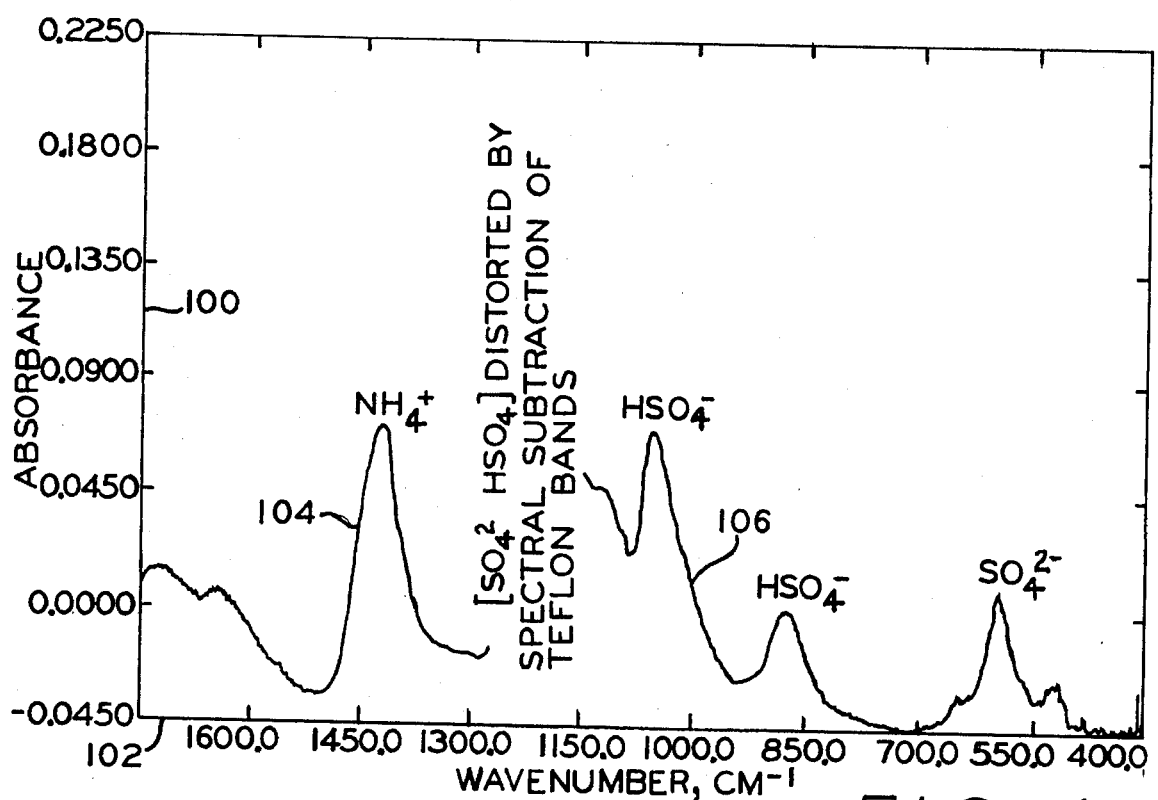
FIG_4
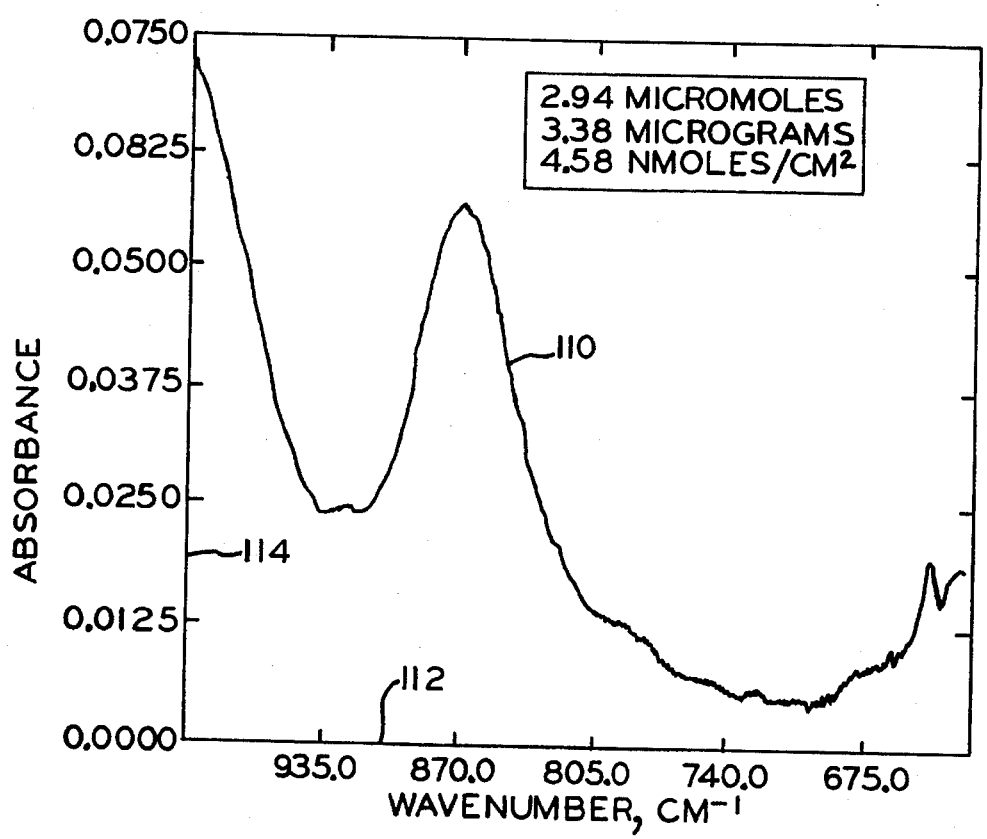
FIG_5

MEASUREMENT OF ACID SULFATE LEVELS IN AEROSOLS

BACKGROUND OF INVENTION

This invention relates to the measurement of acid sulfate levels in an aerosol, such as in ambient air, and in particular to an infrared quantitative measurement method for fine particles such as bisulfate in ammonium bisulfate.

Fine particle sulfates constitute the major source of acid aerosol in the ambient and indoor air. Acid aerosols pose a threat to human health and well-being which has been recognized and which is the basis for recent regulatory control of the precursors for acid aerosol as part of the Clean Air Act Amendments of 1990. However, measuring the existence and levels of acid sulfate in air has proven to be difficult and remains the subject of continuing research which is necessary to establish a scientific basis for regulatory action in protecting persons exposed to acid sulfate in air.

One method for determining particle acidity involves the collection of acid particles on a filter and the water extraction of the particles for analysis of hydrogen ion, ammonium ion, sulfate ion and other ions by, for example, ion selective electrode or ion chromatography. The acidity is often associated with the total concentration of hydrogen ion although the chemical species from which the hydrogen ion is extracted is invariably in question. These methods do not allow speciation of sulfate into ammonium sulfate, ammonium bisulfate and sulfuric acid. This distinction is important because each species of sulfate has different potential health effect. Also, present measurement methods are not fully satisfactory in a number of respects and in meeting present needs as discussed further below. In particular, it is highly desirable that the measurement method sample can be preserved for additional, complementary analyses such as X-ray fluorescence, or wet chemical analyses. Moreover, it is desirable to be able to detect and to provide a numerical value related to acid sulfate in the particle sample at the relatively low concentration levels routinely present in the ambient atmosphere.

OBJECT AND SUMMARY OF INVENTION

It is an object of the present invention to provide a method for the measurement of the bisulfate ion in ammonium bisulfate in particulate samples collected from ambient air, or from concentrations established or existing in air, onto filters.

Another object of the present invention is to provide an improved method for the measurement of acid sulfate levels and concentrations in air which is non-destructive of the sample being measured.

It is still another object of the present invention to provide an improved method for the measurement of acid sulfate levels and concentrations in air which is capable of detecting and measuring low-levels of acid sulfate.

It is yet another object of the present invention to provide an improved method for the measurement of acid sulfate levels and concentrations in air which is capable of measuring the bisulfate level of ammonium bisulfate in a particular sample and to unambiguously distinguish ammonium bisulfate from ammonium sulfate.

It is an additional object of the present invention to provide an improved method for the measurement of acid sulfate levels and concentrations in air which is accurate and reliable, and yet which can economically be implemented with equipment that is small in size, lightweight and capable of field use.

In accordance with one form of the invention, infrared ambient measurements of Teflon filters are made before and after particle collection on the filter resulting from air flow through the filter with bisulfate measurements at approximately 870; 1050; and/or 1125 $cm^{-1}$ wavelength, the prominent absorption bands. The absorption band centered at 870 $cm^{-1}$ is calibrated for the bisulfate ion utilizing calibration standards, and measurements are made of the infrared energy absorption of the selected wavelength by the filter both before and after at least a portion of the aerosol is flowed through the filter for a finite period of time. The difference between the first measurement and the second measurement provides a differential measurement which is an indication of the presence and amount of ammonium bisulfate in the air flow.

More particularly, a collection period may be extended to enable the measurement of relatively low levels of ammonium bisulfate. A Teflon filter is utilized for the sample collection. The method is sensitive to the ammonium bisulfate in the total sulfate collected and calibration standards can be synthetically generated.

DESCRIPTION OF DRAWINGS AND INVENTION

FIG. 1 is a diagram of the field equipment utilized in the present invention.

FIG. 4 shows the infrared absorbance spectrum of various functional groups found in samples of ambient aerosols.

FIG. 5 illustrates the main absorption peak for bisulfate in ammonium bisulfate.

FIG. 6 illustrates the capability of the present invention in measuring ammonium bisulfate compared with direct hydrogen ion measurements.

Figure 2:
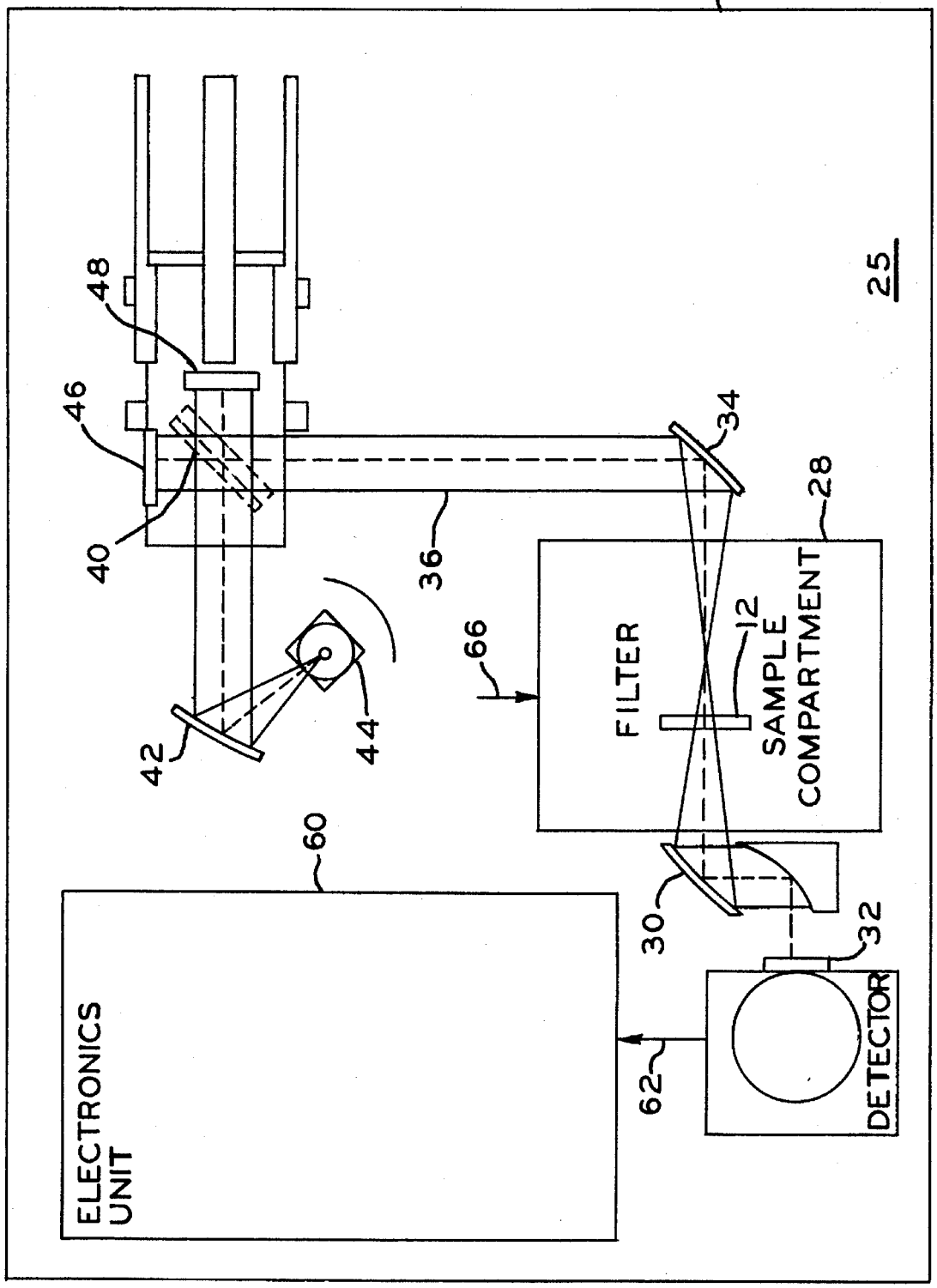
FIG. 2 is a schematic showing the bench or laboratory equipment utilized in the present invention.

Referring first to FIG. 1, air sampler 2 suitable for acid sulfate sample collection in the field, includes inlet pipe 4 through which air or aerosol sample 3 being collected is passed to cyclone 6. Cyclone 6 causes size fractionation of particles in the air sample with larger particles remaining in the cyclone and small particles moving downstream with the air flow. The air flow is directed past the threaded coupler 8, through an annular denuder which is coated with citric acid for removal of basic gases including ammonium, and then through an inline Teflon filter. The particles in the air stream are collected on the inline Teflon filter. The air flow continues past the quick disconnect assembly 16 to outlet 18 which is connected to a flow controller and/or flow meter 1 and vacuum pump 20. Vacuum pump 20 provides the vacuum for drawing air sample 3 through the sampling system. The inline filter 12 is a 37-mm diameter, 2-um pore size PTFE Teflon filter sold by Gelman Sciences, Inc., Ann Arbor, Mich. Flow meter 1 provides a measure of the quantity of the air flow in the sample being measured.

Acid sulfate collector 2 is readily transportable and suitable for field use with the quick disconnect assembly 16 and threaded coupler 8 enabling ready disassembly of the apparatus for removal of the inline filter 12 for subsequent measurement on the equipment of FIG. 2 after the air flow 3 has been continued for the desired finite period of time. The assembly is enclosed within housing 10 with heating means 11, illustrated schematically by variable resistor 7 providing an internal temperature at 4 degrees C. above the ambient temperature to prevent condensation of water vapor on annular denuder 9 and filter holder 14.

Inline filter 12 is conveniently secured in place by snap rings (not shown) to hold the filter surface taut and in position within the system both in acid sulfate collector 2 and subsequently for non-destructive analysis in the FT-IR (fourier transform infrared)—based absorption equipment described below in connection with FIG. 2.

Air sample flow 3 impinges on and passes through filter 12 for an extended period of time, which period may range from two to three hours to several days, or even several weeks, with the air flow being measured and controlled by flow meter 1 to enable time integrated measurements. Filter 12 is then removed and the amount of ammonium bisulfate embedded in the filter measured by placing the filter in the measuring apparatus shown in FIG. 2.

Referring next to FIG. 2, FIG. 2. is a schematic showing the FT-IR (fourier transform infrared) optical bench or laboratory apparatus utilized for infrared measurements of filter 12. Positioned on bench 26 is sample compartment 28 designed to receive filter 12 for measurement both before and after exposure to air sample 3 in acid sulfate collector 2. The interior of housing 26 is purged with dry nitrogen to minimize spectral interference from permanent atmospheric gases and to dry the aerosol. Detector 32 provides non-destructive analysis by infrared (hereinafter IR) absorption of source radiation by particles on filter 12. Input mirror 42 collimates an infrared beam from IR source 44 to pass through the interferometer including IR beam spitter 40, fixed mirror 46 and movable mirror 48 to pass to beam focusing mirror 34 and to then pass through filter 12 onto sample mirror 30 and deuterated triglycine sulfate detector 32 operated at room temperature. The equipment incorporates the Nicolet Model 5 DBX FTIR Interferometer equipment. Electronic unit 60 which is part of that equipment receives output signal 62 and provides the fourier transform IR-based calculations and indications of the IR absorption on filter 12. That is, it measures the level of acid sulfate in filter 12 and in particular the amount of ammonium bisulfate. Measurements of the IR energy adsorbed by filter 12 is centered in a band having a wavelength of 870 cm$^{-1}$. Wavelengths of 1050 cm$^{-1}$ and 1215 cm$^{-1}$ which are also responsive to ammonium bisulfate may also be utilized.

In operation, filter 12 is initially placed in sample compartment 28 before sampling and IR energy absorption across the selected wavelength band is measured to determine the blank value of ammonium bisulfate after the sample compartment has been purged by nitrogen purge 66. Filter 12 is then sealed and transported to the field for use in acid sulfate collector or sampler 2 shown in FIG. 1. Sampler 2 is then exposed to the air being measured, being positioned, for example, 3 to 30 meters above ground level for a period of time which may extend from 2–3 hours to a full day as measured and indicated by a clock or timer. While times up to 23 hours have been tested, and longer integrated measurements provide better accuracy, particularly of low or variable levels of acid sulfate, an exposure in the order of eight hours should normally be adequate for most locations. Filter 12 is then removed and sealed for transportation to FTIR bench unit 25 where it would be inserted into sample compartment 28 as shown in FIG. 2 for measurements of the ammonium bisulfate level after exposure to air in the field or area being tested. To insure the integrity of field samples a special shipping container for filter 12 has been used. Filters were enclosed in small plastic containers which were placed inside a second plastic container lined with tissue impregnated with a mild solution of citric acid. This procedure was used to remove gaseous ammonia from the air surrounding the filter and thereby preserve any acid aerosol.

With knowledge of the rate of air flow 3 which has passed through filter 12 as indicated by flow meter 1 in FIG. 1, and knowledge of the time period of exposure of filter 12 to the air flow as indicated by a timer or clock (not shown) it is possible to calculate total air volume by multiplying the former by the latter which is then used to calculate ammonium bisulfate concentration, or average ammonium bisulfate concentration, during the period of measurement.

The calculations is as follows:

$$\text{Acid Sulfate Concentration} = \frac{M_2 - M_1}{t \times f}$$

where $M_1$=initial measurement $M_2$=measurement after sample collection f=flow rate in liters t=time in hours By way of example of the above calculation, if flow rate f by flow meter 1 is set at 10 liters per minute, 13.8 cubic meters of ambient air will be collected and passed through filter 12 during a period of 23 hours. If, in the example given, acid sulfate level is measured by FTIR bench unit 25 initially as 2 micrograms while the level measured at the end of the 23 hour exposure is 50 micrograms then the acid sulfate concentration of the air being sampled by sampler 2 is 50–2 or 48 micrograms for the 23 hours divided by 13.8 cubic meters which equals 48/13.8 or 3.48 micrograms per cubic meter. That is, the concentration is determined on the basis of the amount of acid sulfate per cubic meter or other convenient unit of measurement.

A calibration response for the system was obtained by measuring the absorbance of standards prepared with a TSI Model 3706 aerosol generator and sampled from a manifold using an in-line filter pack. Standard filters were loaded with ammonium bisulfate ranging from 85 ugm to 350 ugm each. The absorbance spectrum was taken from 4000 to 400 cm$^{-1}$ and the area centered at 870 cm$^{-1}$±36 cm$^{-1}$ was integrated for the bisulfate measurement. The filters were then extracted with 20 ml of water using ultransonification for 60 minutes. A 0.5 ml aliquot of the sample was then analyzed using an Orion Model 511 ion selective electrode for direct determination of hydrogen ion. A calibration curve 96 was then obtained (See FIG. 6). Measurements of sulfate were also made on a Dionex Model 4000 ion chromatograph 94 (FIG. 6). Since the measurements of sulfate was considered very reliable, sulfate was used as a surrogate for hydrogen ion. Based on the respective slopes, the calibration curve generated from the direct determination of hydrogen ions 96 is on average 10.6% lower than the hydrogen ion calibration curve generated from equivalent sulfate ion values 94. The lower limit of detection (LLD) was then computed from calibration curve 96 as having a 3/1 signal to noise ratio. The LLD corresponds to a collected sample weight of 17.3 µg of ammonium bisulfate on a standard 37 mm filter made of polytetraflluoroethylene such as that manufactured and sold as Teflon by E. I. Dupont de Nemours and company.

Figure 3:
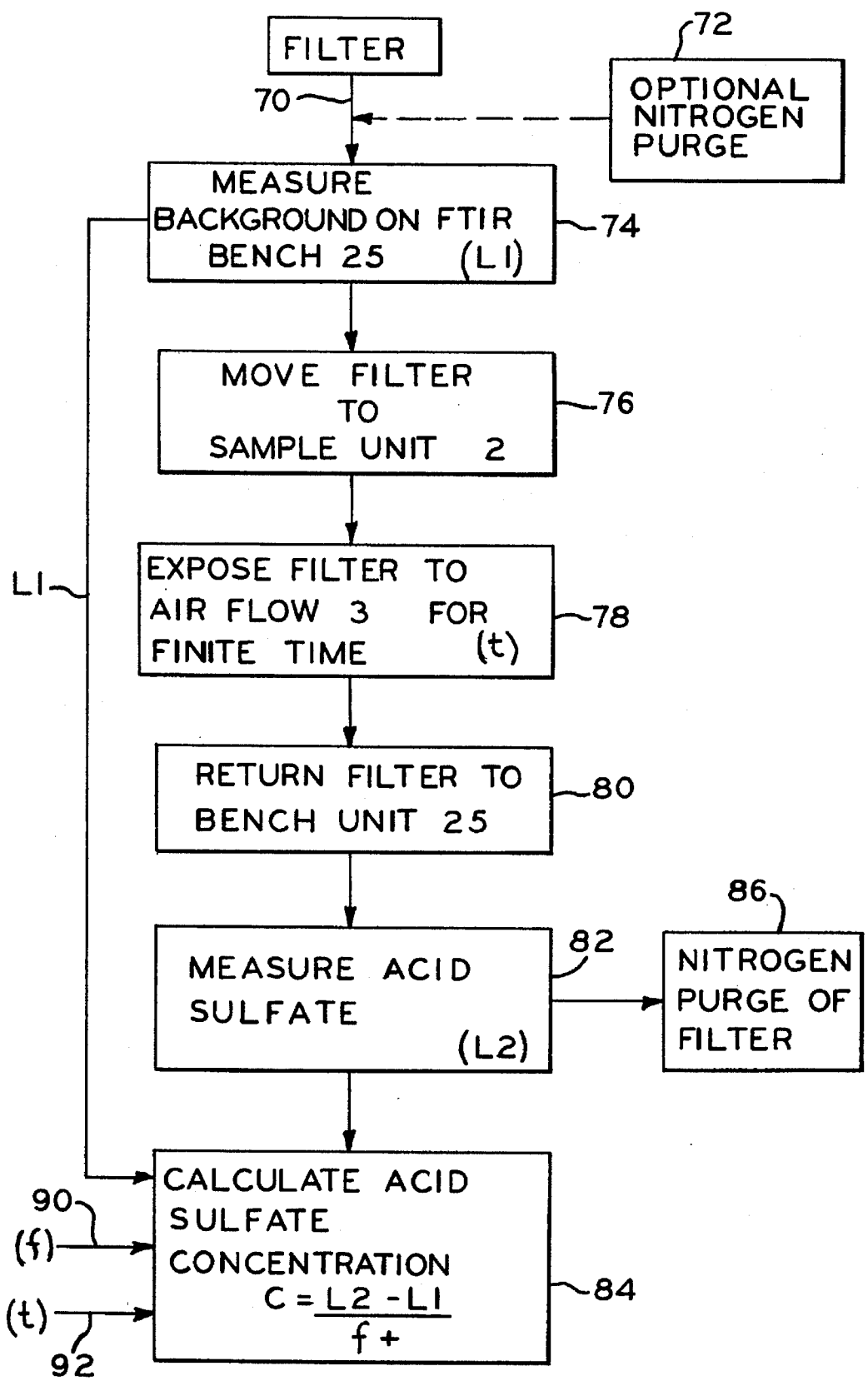
FIG. 3 is a block diagram useful in explaining the measurement method of the present invention.

By way of summary and further explanation, the measurement procedure is illustrated schematically in FIG. 3.

Referring to FIG. 3, filter 12 is positioned 70 on bench 25 in sample compartment 28 where it may be subjected to optional nitrogen purge 72 and the acid sulfate level L1 of filter 12 is measured 74 by IR absorption on the bench across the ammonium bisulfate band centered at 870 cm$^{-1}$. Filter 12 is then sealed and moved 76 to sample unit 2 which is positioned at a location where ambient air samples are to be collected. The location can be outside or in a factory. Filter 12 is then exposed 78 to air flow 3 (See FIG. 1) for a finite period of time t. After removal and wrapping for protection, filter 12 is returned 80 to bench unit 25 where the acid sulfate level is again measured 82 by FT-IR equipment 25 to provide measurement L2. Bench 25 measures the acid sulfate levels by FT-IR energy absorbance at a band centered at a wavelength of 870 cm$^{-1}$ plus or minus approximately 40 cm$^{-1}$ and/or at wavelength of 1050 cm$^{-1}$ or 1215 cm$^{-1}$ plus or minus 40 cm$^{-1}$. The spectral regions used are relatively free of interference from Teflon absorption and from most other species. There is a small displacement of the sulfate absorption band as a function of acidity. However, the 40 cm band adequately covers the displacement band. The acid sulfate concentration is then calculated 84 utilizing electronics/computer unit 60 through utilization of the L1 level provided by measurement 74, the L2 measurement provided by 82, the flow measurement 90 provided by flow meter 1 in FIG. 1, and elapsed exposure time 92 provided by a timer.

FIG. 4 shows a plot of the absorbance of ambient air particulate seen in a typical environment. The sample was collected on Teflon filter 12. Infrared absorbance was plotted on Y axis 100 and wavelength in cm$^{-1}$ on X axis 102. It is to be noted that NH$_4$+ peaks occur around 1450$^{-1}$, HSO$_4$ peaks at around 1025$^{-1}$, and 870 cm$^{-1}$, and the SO$_4^{2-}$ at around 600 cm$^{-1}$. Also the spectral region for Teflon is around 1,150–1,300 cm$^{-1}$, accounting for the break between absorption plots 104 and 106. FIG. 4 also shows that the quantitation of ammonium bisulfate in accordance with the present invention is performed in a spectral region or wavelength using an integrated area at 870 cm$^{-1}$ which is free from the overlapping spectra bands from Teflon absorption, and from most other acid species. Fine particle nitrate absorbs at or near 830 cm$^{-1}$, the exact position depending of the presence of particulate species that alter the bond strength. The integrated area centered at 870±36 cm$^{-1}$ is thus used for qualitative and quantitative purposes. Matrix effects can shift the center of the bisulfate band over a range of approximately 872 to 867 cm$^{-1}$. In all cases the center of the band ±36 cm$^{-1}$ is used for integration. The area is measured and compared to a calibration curve to obtain the amount of bisulfate present in the sample.

FIG. 5 shows that the absorbance peak 110 and calibration for ammonium bisulfate in accordance with the present invention is free of interference from most acid species found in the ambient air acid aerosol. FIG. 5, as in FIG. 4, has wavenumber in cm$^{-1}$ on X axis 112 while absorbance is plotted on Y axis 114.

The calculation 84 involves a fourier transform, and the resultant measurements have been compared with other measurements of acid sulfate levels such as ion-selected electrode analysis. The results verified the accuracy of the subject invention and moreover, the subject invention enables a highly portable, lightweight, uncomplex and relatively inexpensive sampling unit suitable for field measurements, and suitable for convenient testing and measurements of levels of acid sulfate and air at locations to be tested in compliance with environmental standards. The present invention unambiguously distinguishes ammonium bisulfate from ammonium sulfate and thus can distinguish a primary component of acid aerosol.

The comparison of the field testing of the subject invention with other concurrent testing and methods is discussed in detail in the article entitled "Speciation of Ambient Sulfate Particulate Matter Using FT-IR-Based Absorption to Complement Wet Chemical and Thermal Speciation Measurements," by W. A. McClenny, K. J. Krost, E. H. Daughtrey, Jr., D. D. Williams, and G. A. Allen, which appeared in *Applied Spectroscopy*, Volume 48, Number 6, 1994, p. 706, which is hereby referenced for a showing of the advantages of the subject invention.

While the subject invention has been tested for the detection and measurement of ammonium bisulfate levels and concentration, the FT-IR measurements procedure involved could be expanded to other functional groups, such as ammonium, nitrate and total sulfate although a different band or bands for the FT-IR measurements would be utilized.

While the present invention has been described with respect to certain preferred embodiments thereof, it is to be understood that numerous variations in the details of construction, the arrangement and combinations of parts, and the types of materials used may be made without departing from the spirit and scope of the invention.

What we claim is:

1. A direct non-destructive method of measuring acid sulfate levels in fine particulate matter collected on a filter from an aerosol flow comprising:

measuring the infrared energy absorbance in a band centered at a wave number selected to be responsive to ammonium bisulfate on said filter to provide a first measurement of ammonium bisulfate;

collecting the fine particle fraction of said ambient air to be measured for acid sulfate levels through a filter for a finite period of time;

remeasuring the infrared energy absorbance about the selected wave number by said filter to provide a second measurement of ammonium bisulfate; and comparing said first measurement and said second measurement to provide a difference measurement as an indication of the amount of acid sulfate in said aerosol flow.

2. The method of measuring acid sulfate levels of claim 1 wherein said absorbance band selected is approximately 870 cm$^{-1}$ and said filter is polytetrafluoroethylene.

3. The method of measuring acid sulfate levels of claim wherein said indication is utilized to provide an indication of the presence and concentration of acid sulfates in said aerosol flow.

4. The method of measuring acid sulfate levels of claim 3 wherein said period of time extends for a period of 2 hours to one week for measuring low concentrations of said ammonium bisulfate.

5. The method of measuring acid sulfate levels of claim 4 wherein said acid sulfate levels on said filter are determined by subtracting said first measurement from said second measurement.

6. The method of measuring acid sulfate levels of claim 3 including the additional step of measuring flow rate of a portion of said flow during said period of time, and utilizing the rate of said aerosol flow and said amount of acid sulfate to provide said indication of concentration of acid sulfates in said flow.

7. The method of measuring acid sulfate levels of claim 6 wherein said aerosol flow is air to be monitored for the presence of said acid sulfates.

8. The method of measuring acid sulfate levels of claim 3 including the additional step of calibrating the infrared measuring equipment by measuring hydrogen ion concentration for a series of ammonium bisulfate calibration standards.

9. The method of measuring acid sulfate levels of claim 8 wherein ammonium bisulfate standards are synthetically generated.

10. The method of measuring acid sulfate levels of claim 9 wherein the generation of said standards includes an aerosol acid generator.

11. The method of measuring acid sulfate levels of claim 8 wherein said measuring includes the determination of levels of ammonium bisulfate with complementary measurements of ammonium sulfate and hydrogen ions.

12. The method of measuring the acid sulfate levels of claim 3 wherein said band has a band width of plus or minus approximately 40 $cm^{-1}$.

13. The method of measuring acid sulfate levels of claim 1 wherein said wave number is selected from the group consisting of approximately 870 $cm^{-1}$, 1050 $cm^{-1}$, and 1215 $cm^{-1}$.

* * * * *